United States Patent [19]
Haller

[11] Patent Number: 5,993,414
[45] Date of Patent: Nov. 30, 1999

[54] IMPLANTABLE DEVICE

[75] Inventor: Markus Haller, Begnins, Switzerland

[73] Assignee: Medtronic, Inc., Minneapolis, Minn.

[21] Appl. No.: 09/064,728

[22] Filed: Apr. 23, 1998

[51] Int. Cl.$^6$ .......................... A61M 11/00; A61M 37/00; A61K 9/22
[52] U.S. Cl. .......................... 604/93; 604/131; 604/891.1
[58] Field of Search .................................. 604/93, 890.1, 604/891.1, 892.1, 131, 151

[56] References Cited

U.S. PATENT DOCUMENTS

| | | |
|---|---|---|
| 4,966,646 | 10/1990 | Zdeblick . |
| 4,978,338 | 12/1990 | Melsky et al. ............................ 604/93 |
| 5,224,843 | 7/1993 | van Lintel . |
| 5,323,051 | 6/1994 | Adams et al. . |
| 5,495,978 | 3/1996 | Muth .................................... 228/122.1 |

FOREIGN PATENT DOCUMENTS

| | | |
|---|---|---|
| WO 96/25619 | 8/1996 | France . |
| 0 502 222 | 3/1991 | Germany . |
| 0 552 466 | 12/1992 | Germany . |
| 0 540 071 | 9/1992 | United Kingdom . |

OTHER PUBLICATIONS

"Review Packaging of Microfabricated Devices and Systems"—Wen H. Ko (Elsevier—Materials Chemistry and Physics 42 (1995) p. 169–175).

*Primary Examiner*—Ronald Stright
*Assistant Examiner*—Michael J. Hayes
*Attorney, Agent, or Firm*—Thomas F. Woods; Harold Patton; Michael J. Jaro

[57] ABSTRACT

The present invention provides an implantable drug infusion device which features a reliable and leak proof weld joint. The implantable drug infusion device features a hermetic enclosure; a drug reservoir positioned within the hermetic enclosure, a drug handling component, the drug handling component joined with a top surface of a docking station, the drug reservoir joined with a bottom surface of the docking station by a welded joint. The drug handling component typically being a MEMS-type device and fashioned from a silicon-glass or silicon—silicon sandwich. The docking station functions to isolate the thermal stresses created during the formation of the welded joint from the other joints and particularly from the joint between top surface of the docking station and the drug handling component. The thermal isolation function of the docking station is provided through one or more grooves within the docking station, the grooves functioning to separate, in a thermal manner, the top and bottom surfaces of the docking station.

20 Claims, 9 Drawing Sheets

IMPLANTABLE DEVICE

FIELD OF THE INVENTION

The present invention relates to the field of implantable devices and more particularly to an implantable drug infusion device having an improved weld joint between various components of the device.

BACKGROUND OF THE INVENTION

Implantable drug infusion devices are used to provide patients with a constant and long term dosage or infusion of a drug or any other therapeutic agent. Essentially such device may be categorized as either active or passive.

Active drug or programmable infusion devices feature a pump or a metering system to deliver the drug into the patient's system. An example of such an active drug infusion device currently available is the Medtronic SynchroMed programmable pump. Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The Medtronic SynchroMed pump further includes an antenna to permit the remote programming of the pump. Passive drug infusion devices, in contrast, do not feature a pump, but rather rely upon a pressurized drug reservoir to deliver the drug. Thus such devices tend to be both smaller as well as cheaper as compared to active devices. An example of such a device includes the Medtronic IsoMed™. This device delivers the drug into the patient through the force provided by a pressurized reservoir applied across a flow control unit.

Regardless of whether the device is an active or passive drug infusion device, any such devices present challenges to assemble, in a sufficiently hermetic manner while still using biocompatible materials. These difficulties are further magnified when such a device utilizes micro-electrical mechanical systems (MEMS). MEMS typically are extremely small, and further are constructed from a silicon-glass or silicon-silicon sandwich. In particular, to date, the joining of different types of materials necessary for use of MEMS technology in an implantable infusion device has not been feasible using any other joining techniques other than welding. In the extremely harsh and ceaselessly aggressive environment found in the body, epoxies and other glues, while permitting a mechanical joint to be reliably fashioned, have not permitted that same joint to be assembled in a satisfactorily leak-proof or water tight manner. Over time, most joint seals using glues or epoxies have been found to permit vapor or moisture to be passed through the joint. When dealing with implantable electrical devices, such vapor can have serious, if not catastrophic, consequences. Thus, to date, the use of welds is found to be the most effective method for joining similar as well as disparate materials together in order to assemble the implantable infusion device.

Welding, however, is often difficult to implement when joining different or disparate materials together. Namely, thermal stresses often result through the heating and the cooling of these materials, such stresses often having unintended or unacceptable consequences with regards to other areas of the device. With particular regards to drug infusion devices, it has been a problem to reliably join a drug reservoir to the other fluid handling components through welding. One area where this problem exists in the joining of the drugs reservoir to such a MEMS device. As mentioned above, MEMS typically are of a sandwich construction, and thus the direct welding of a component to them is not possible. Often, it has been necessary to use or more intermediary layers to achieve a bond to the MEMS but which may, in turn later be welded to the drug reservoir, for example. During the weld process, however, often the thermal stresses have caused the joint to be formed with one or more flaws, i.e. buckling (when welding thin membranes), delamination (when welding thin film), cracking (of glasses due to stresses introduced when welding).

It is, thus, the object of the present invention to provide a drug infusion device which permits such a drug reservoir to be coupled to the fluid handling components through welding.

SUMMARY OF THE INVENTION

The present invention provides an implantable drug infusion device which features a reliable and leak proof weld joint. The implantable drug infusion device features a hermetic enclosure; a drug reservoir positioned within the hermetic enclosure, a drug handling component, the drug handling component joined with a top surface of a docking station, the drug reservoir joined with a bottom surface of the docking station by a welded joint. The drug handling component typically being a MEMS-type device and fashioned from a silicon-glass or silicon-silicon sandwich. The docking station functions to isolate the thermal stresses created during the formation of the welded joint from the other joints and particularly from the joint between top surface of the docking station and the drug handling component. The thermal isolation function of the docking station is provided through one or more grooves within the docking station, the grooves functioning to separate, in a thermal manner, the top and bottom surfaces of the docking station.

The FIGS. are not necessarily to scale.

DETAILED DESCRIPTION OF THE DRAWINGS

As discussed above the present invention relates to the ability to weld together biocompatible materials and create a reliable and leak proof joint. The present invention is directed especially to the problem of creating such a leak-proof joint while interfacing with a MEMS-type component within an implantable drug infusion device. As discussed in more detail below the present invention creates such a leak proof joint through the use of a docking station capable of being attached to both a MEMS-type component while further being able to be welded to a another component. The docking station is designed so as to handle, without passing through to other joints, the thermal stress created during the weld process. This unique design for the docking station thus provides for a drug infusion device which permits at least two of the components (where at least one is a MEMS-type component) to be joined in a sealed and hermetic fashion by welding.

Figure 1:
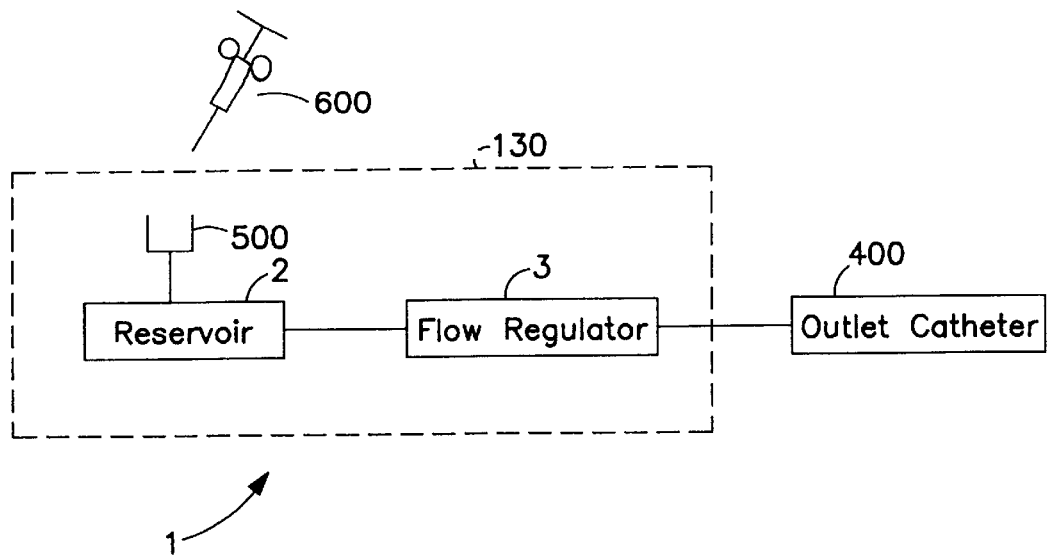
FIG. 1 is a block diagram of an implantable drug infusion device and in particular of a passive system to deliver drugs and other therapeutic agents.

FIG. 1 generally illustrates an implantable drug infusion device and in particular is a block diagram of a passive system to deliver drugs and other therapeutic agents. As seen, such a system 1 comprises a reservoir 2, fluid handling device, depicted here as flow regulator 3 and outlet catheter 400. The reservoir is a pressurizable reservoir to hold drugs and other therapeutic agents. Reservoir may be of a standard design, such as that used in the above mentioned Medtronic IsoMed™ implantable drug infusion system. Flow regulator 3 is coupled to the reservoir and the outlet catheter. Flow regulator controls the flow of material which may be transmitted from the reservoir to the outlet catheter and in particular permits the flow rate to be independent of reservoir pressure within a given pressure range. System may be refilled through injection port 500 through the use of a needle 600 as is well known. Surrounding all components of the implantable pump other than the outlet catheter is a hermetic closure 130 as is well known in the art. Preferably this hermetic enclosure is fashioned by matching titanium can halves which are welded together so as to seal in a hermetic manner the enclosure in the can from the exterior. While this illustration depicts one type of drug infusion device within which the present invention may be practiced, it may also be practiced in other types of drug infusion devices, such as active devices which feature a pump, as well as in any other type of implantable device which requires a the ability to weld together materials and create a reliable and leak proof joint. Such device may included, for example, medical electrical stimulators.

Figure 2:
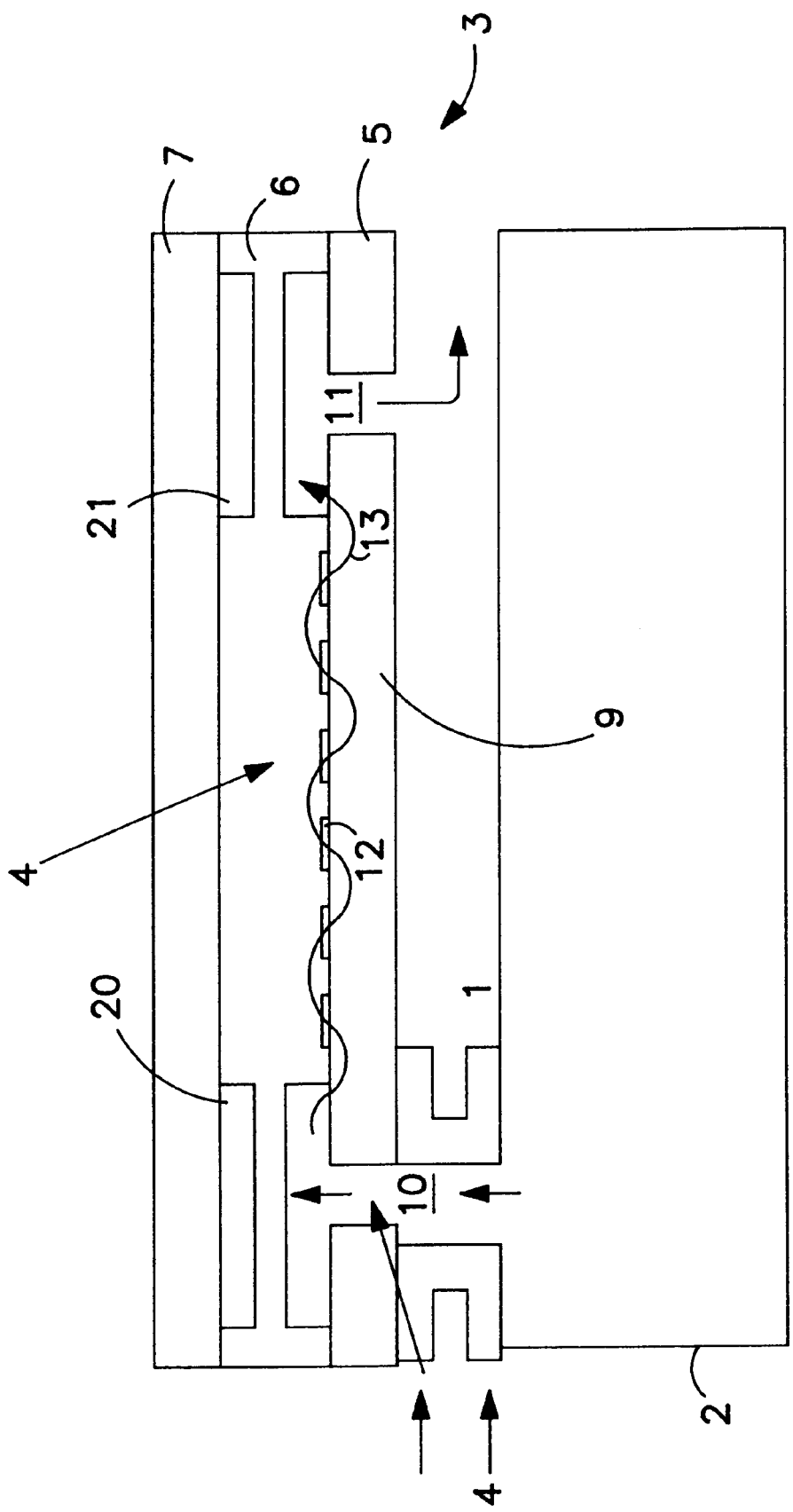
FIG. 2 is a sectional view of a drug infusion device according to the present invention.

FIG. 2 is a sectional view of a drug infusion device according to the present invention. In particular, FIG. 2 depicts a drug reservoir 2 coupled to a fluid handling component 3 through a docking structure 4. Docking structure 4 is necessary because of the materials used in component 3. Namely, component 3 is structured so as to be biocompatible and further to minimize the interaction of any fluid or drug infused from the reservoir into the body, i.e. it is structured using materials that are highly inert as compared to materials that are interactive. The fluid handling component 3 depicted has a flow restrictor in between two pressure sensors, that form a flow sensor system in total, although the present invention may be used with many other types of fluid handling components. The flow restrictor is merely shown in the present invention to illustrate the drug infusion device component to which the present invention may be used. As seen, fluid handling component 3 is a multi-layer assembly of base substrate 5, middle substrate 6 and top substrate 7. Base and top substrates are preferably of glass or silicon while middle substrate is preferably made of silicon. Base substrate features an inlet 10 and an outlet 11. Inlet and outlet are in fluid communication via a torturous path defined between channel 12 in middle substrate and the upper surface of base substrate. In the present example torturous path is further illustrated by arrow 13. Cavity 20 is provided over inlet while cavity 21 is provided over outlet. Middle substrate is fashioned so as to deflect through the presence of pressure at inlet, such deflection resulting in a capacitive change across cavity 20. Presence of pressure at outlet, such deflection resulting in a capacitive change across cavity 21. The flow restrictor induces a pressure drop proportional to the flow across the flow restrictor. Following the general equation:

$$\Delta p = R * Q$$

where R=Flow Resistance [(Pa*s)/m$^3$], $\Delta$p=Pressure Drop [Pa], Q=Flow [m$^3$/s] and:

$$R = (128 * \mu * L)/(\pi * D^4)$$

where R=Flow Resistance [(Pa*s)/m$^3$], $\mu$=10$^{-3}$ [kg/(m*s)], L=Channel Length, D=Channel Diameter.

For the specific geometry of this semicircular Channel design this equation is then:

$$R = (13.443 * \mu * L)/r^4$$

with:

R=Flow Resistance [(Pa*s)/m$^3$], $\mu$=10$^{-3}$ [kg/(m*s)], L=Channel Length, r=radius of semicircle. In such a manner the pressure drop between inlet and outlet may be measured and through this the fluid flow rate may be determined, as is well known in the art. The particular details of fluid handling component, as described above, is merely to illustrate one combination to which the method and docking structure of the present invention may be used.

Figure 3:
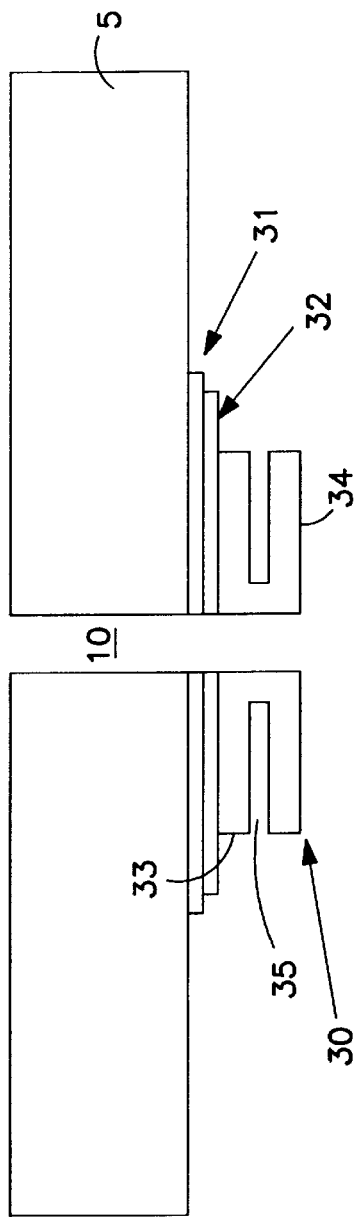
FIG. 3 is a sectional view of the docking structure according to the present invention.

FIG. 3 is a sectional view of the docking structure according to the present invention. As seen, base 5 is coupled to docking structure 30 through first layer 31 and second layer 32. These layers may be applied to the base by sputtering, evaporating, plating or by using a pre-formed layer for the layer 32. As described above, base substrate is preferably glass while, in this embodiment, first layer 31 is titanium, second preferably pre-formed layer 32 is gold and docking structure 30 is titanium. Of course, the particular materials used depend upon each of the other materials which are selected. It is preferred, however, that both the first layer and the docking structure be of the same material so that any thermal stress induced by one of the structures will, by some degree, be compensated by a similar thermal stress in the opposite structure. The method of attaching first pre-formed, second pre-formed and docking structure are all disclosed further with regards to FIG. 9. As seen in this view, docking structure 30 features a first planar surface 33 and a second planar surface 34 to which a subsequent component, such as a drug reservoir, may be welded. As seen, one of the essential features of docking structure is a physical separation via a groove or slot located preferably midway between first surface 33 and second surface 34. As discussed above, this groove or slot 35 permits the thermal stresses which are induced during the welding of second surface 34 to a component to be isolated from the join formed between first surface 33 and second pre-formed layer 32. Although groove is located preferably midway between surface of docking structure, groove may also be located in other locations, such as closer to either of the planar surfaces.

Figure 4:
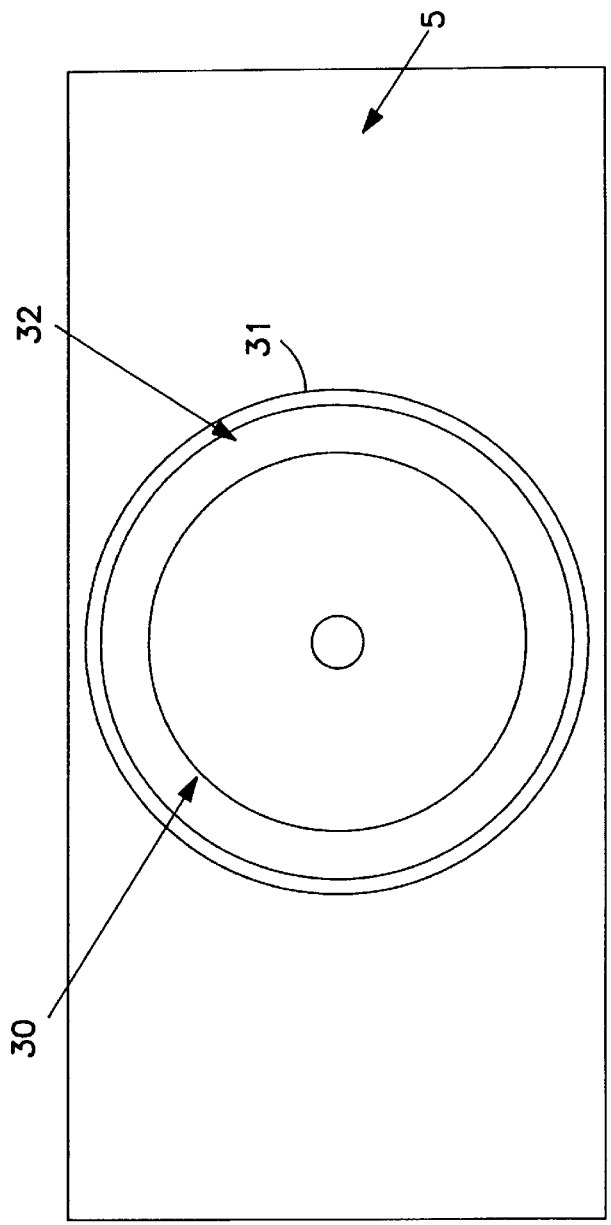
FIG. 4 is a bottom view of the components shown in FIG. 3.

FIG. 4 is a bottom view of the components shown in FIG. 3. As seen in this view, first layer 31, second pre-formed layer 32, docking structure 30 as well as inlet 10 are all circular in shape. Of course, other shapes may also be used and still be within the scope of the present invention, such as shapes including square, elliptical, irregular or any other shapes.

Figure 5:
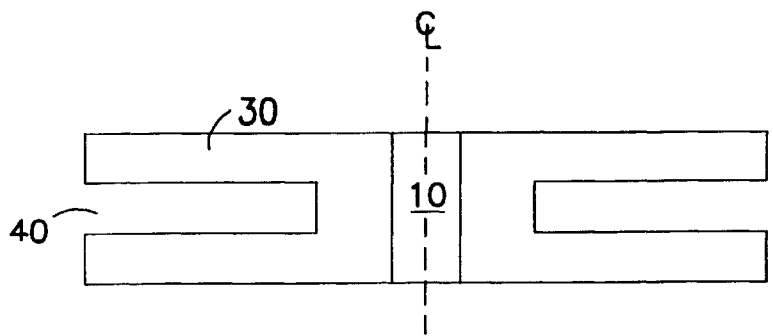
FIGS. 5–8 show, in isolation, an alternative embodiment for docking structure which may be used in the present invention.

FIG. 5 shows, in isolation, an alternative embodiment for docking structure which may be used in the present invention. In this embodiment, docking structure 30 features a square groove 40.

Figure 6:
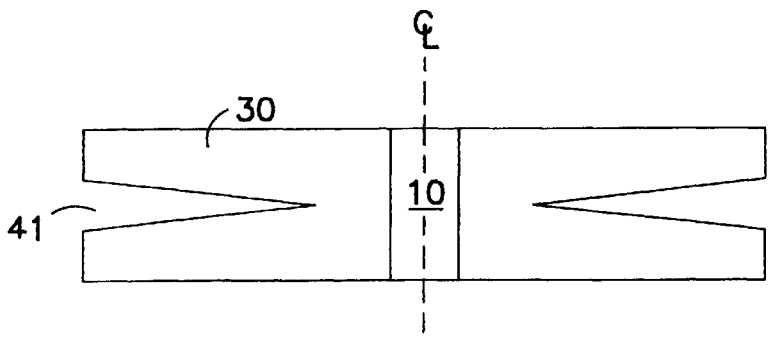

FIG. 6 shows, in isolation, an alternative embodiment for docking structure which may be used in the present invention. In this embodiment, docking structure 30 features a V-groove 41.

Figure 7:
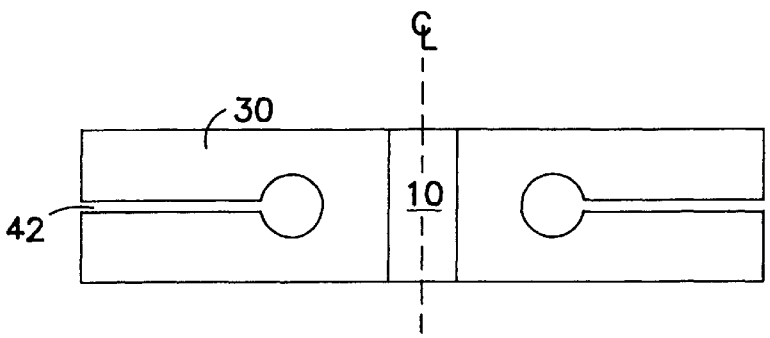

FIG. 7 shows, in isolation, an alternative embodiment for docking structure which may be used in the present invention. In this embodiment, docking structure 30 features a spoon groove 42.

Figure 8:
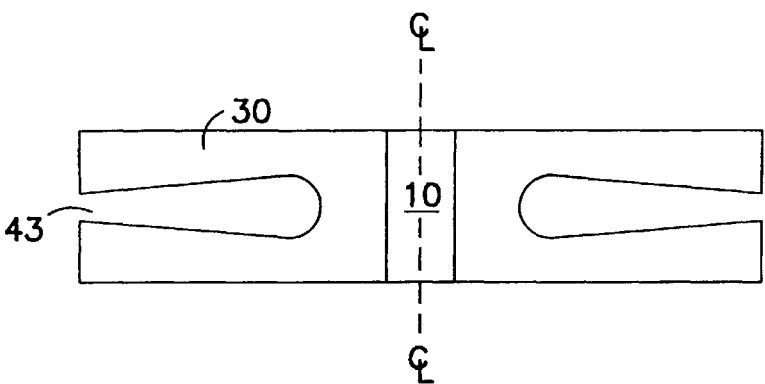

FIG. 8 shows, in isolation, an alternative embodiment for docking structure which may be used in the present invention. In this embodiment, docking structure 30 features a club groove 43.

Figure 9:
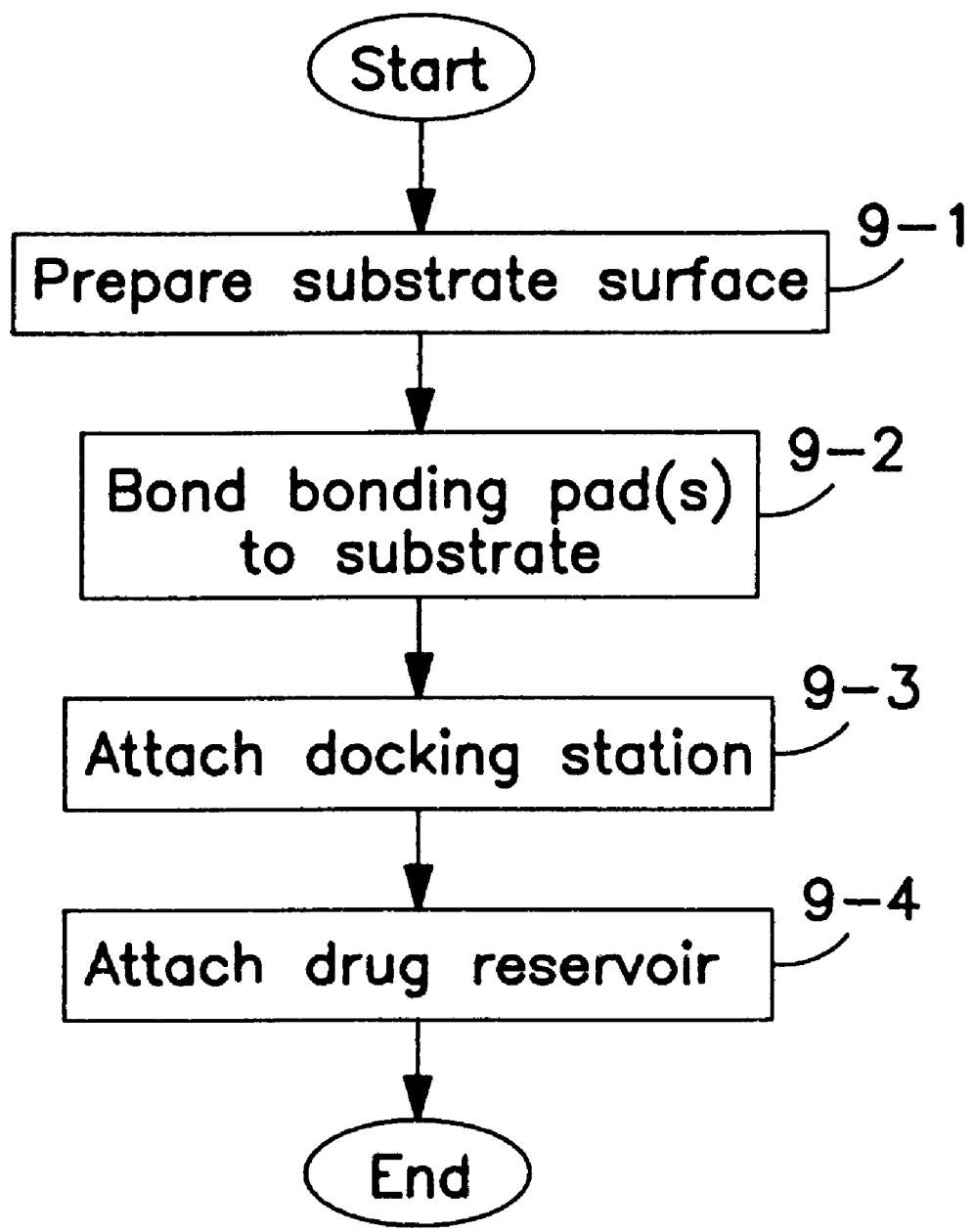
FIG. 9 depicts the method through which an implantable drug infusion device may be assembled according to the present invention.
Figure 10A:
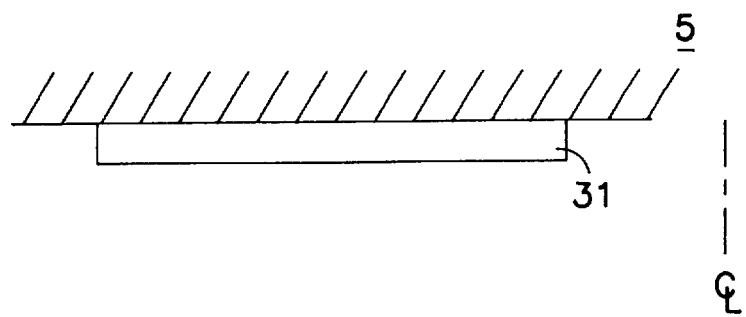
FIG. 10 illustrates the steps used to join a substrate to a drug reservoir using the docking station.
Figure 10B:
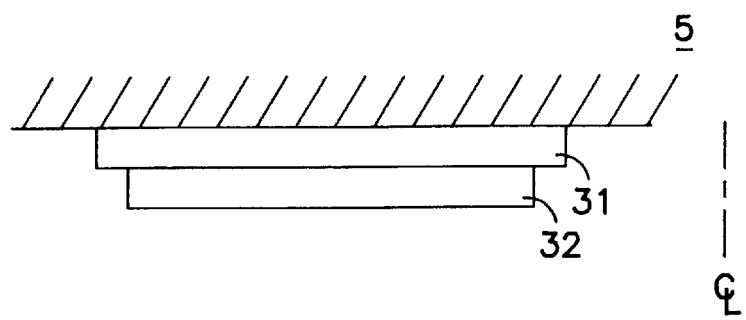
Figure 10C:
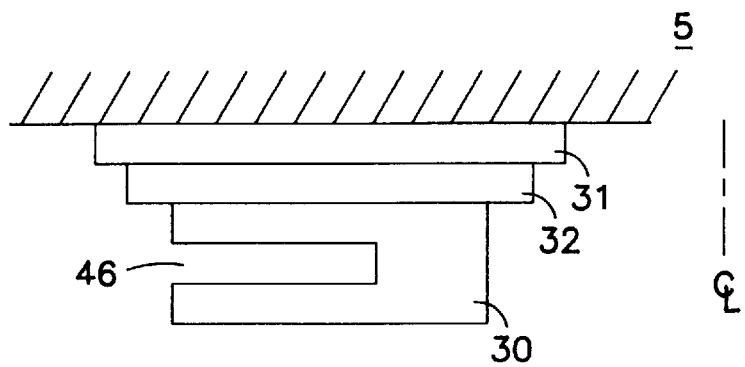
Figure 10D:
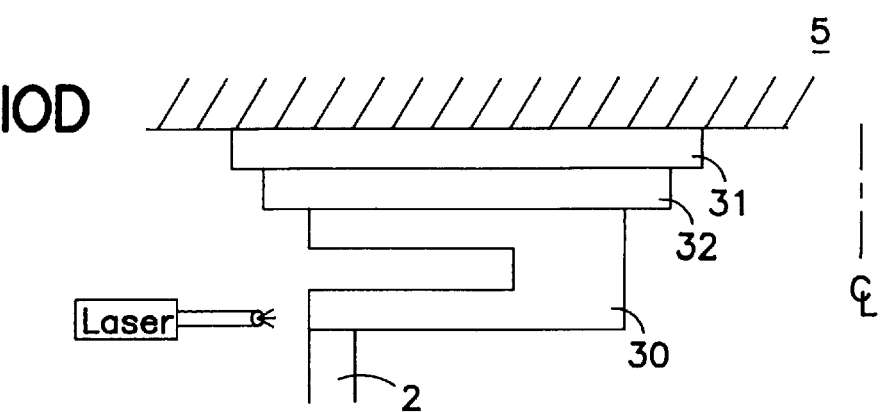

FIG. 9 depicts the method through which an implantable drug infusion device may be assembled according to the present invention. As seen in the first step the substrate to which the docking station is to be mounted has its surface 50 prepared. Next one or more bonding strips are bonded to the surface. As explained in more detail below the bonding strips assist in the joining of the docking station to the substrate. Once boding strips are bonded to the substrate the docking station is affixed to a bonding strip, and thus to the substrate. Finally, drug reservoir is welded to the docking station. Of course, the exact steps utilized, depend, to a great deal, upon the materials involved. It should be contemplated that one or more of these steps may be skipped, if possible.

FIG. 10 illustrates the steps used to join a substrate to a drug reservoir using the docking station. As seen, in FIG. 10A a first bonding pad 50 is affixed to the substrate surface by evaporation. Fixation may be accomplished using standard CVD or LPCVD (chemical vapor deposition) techniques. Next as seen, in FIG. 10B, a second bonding pad is affixed to surface of the first bonding pad preferably using Standard Gold Electroplating or Standard Gold Sputtering techniques. Sputtering is performed in an Argon atmosphere at 2.5 to 12.5 PA pressure and around 400 eV activation energy. Next as seen, in FIG. 10C the docking station is affixed to the second bonding pad by brazing (at temperatures between 500 and 700° C. at ambient pressures). Finally as seen, in FIG. 10D, a drug reservoir is affixed to the docking station by a standard laser welding technique. In the preferred embodiment substrate is made of Pyrex glass, first bonding pad is made of titanium, second bonding is made of gold, docking station is made of titanium; and drug reservoir is made of titanium. Of course each of the components may be fashioned from any other acceptable and suitable materials, including those requiring different affixation techniques. For example a first bonding pad could also be made using tantalum and affixed to substrate through gold while second bonding could also be made using tantalum and affixed to first bonding pad using gold Docking station could also be made of tantalum affixed to second bonding pad using gold.

Figure 11:
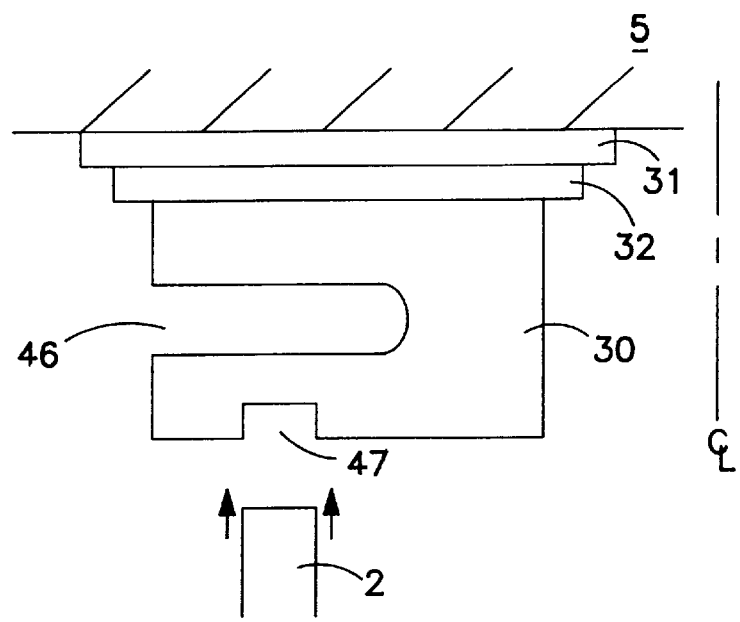
FIG. 11 shows, in isolation, an alternative embodiment for docking structure which may be used in the present invention.

FIG. 11 shows, in isolation, an alternative embodiment for docking structure which may be used in the present invention. In this embodiment docking structure 30 features an additional alignment groove 47. As seen, alignment groove permits drug reservoir (or whatever other component is to be mated into docking structure) to be easily and precisely positioned.

Figure 12:
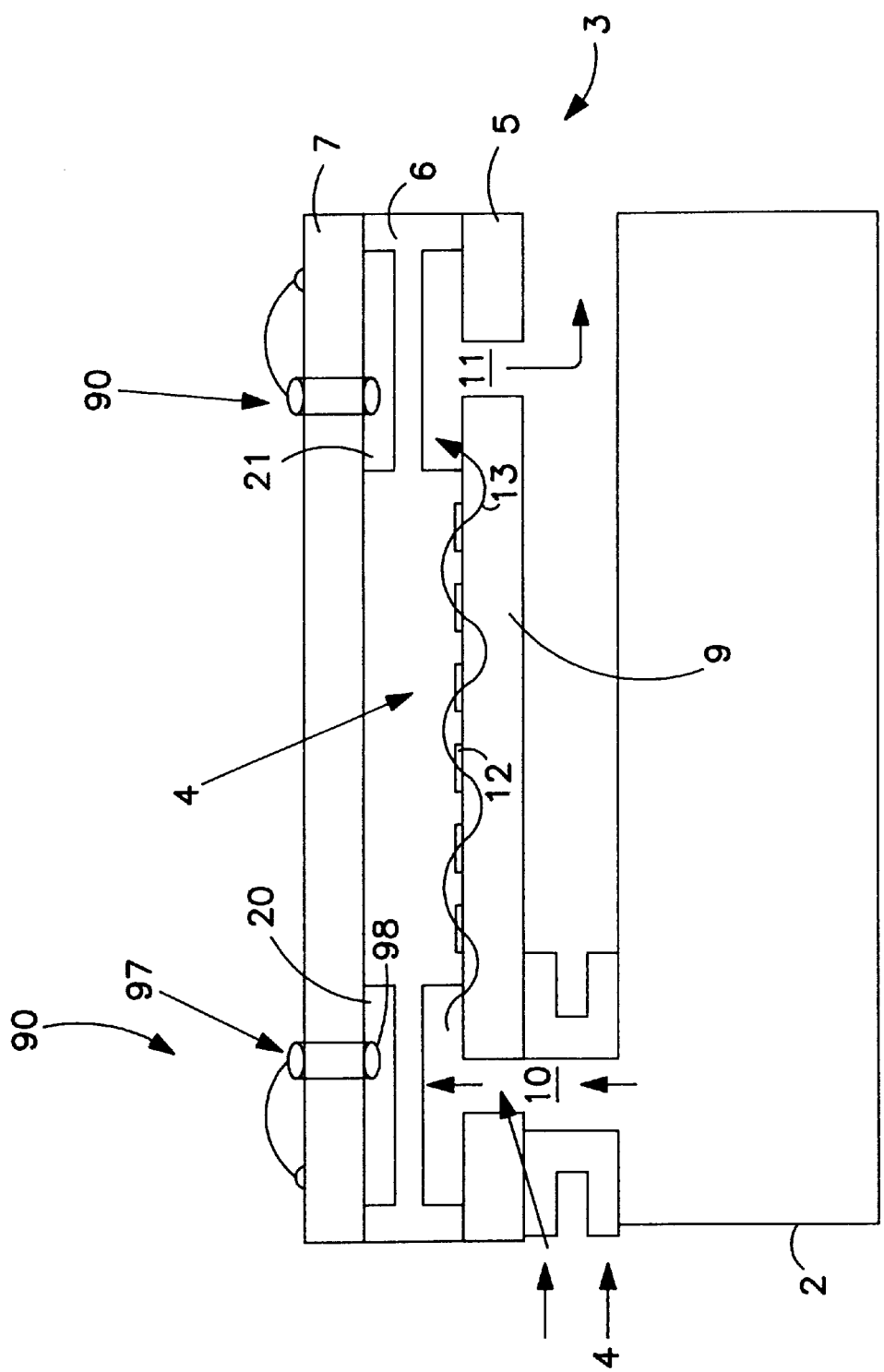
FIG. 12 is a sectional view of a further alternative embodiment of a drug infusion device according to the present invention.

FIG. 12 is a sectional view of a further alternative embodiment of a drug infusion device according to the present invention. As seen, this embodiment is substantially similar to that shown in FIG. 2 but for the additional provision of one or more electrical feed-throughs 90. As seen, feed-through is fashioned through a tungsten via 96 which is gold ball bump 98 which serves as one side of the connection while a second gold ball bump 97 is on the other side of the connection. As seen, gold ball bump 97 may further feature a wire bond to provide ready electrical connection. Preferably the bonding process of the top substrate and middle substrate will occur via a hermetic epoxy sealing process at a temperature at which the two gold ball bumps will bond together.

Figure 13:
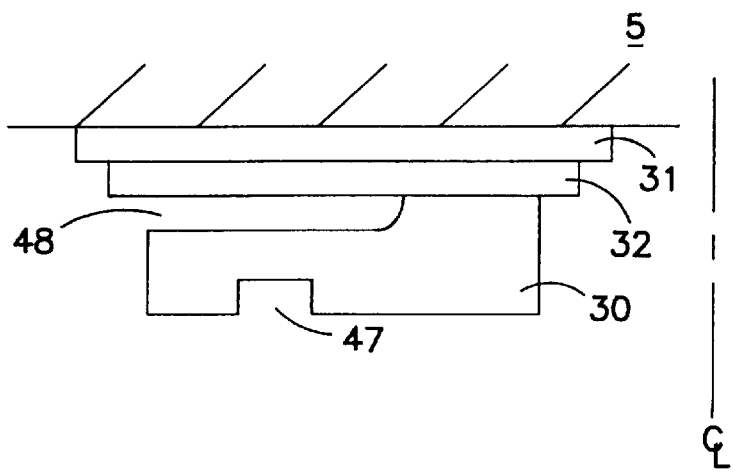
FIG. 13 shows, in isolation, an alternative embodiment for docking structure which may be used in the present invention.

FIG. 13 shows, in isolation, an alternative embodiment for docking structure which may be used in the present invention. In this embodiment, docking structure 30 features a groove 48 positioned at the top surface such that the docking station has less surface area along its top surface to bond to substrate than compared to if the groove was located within docking station.

Figure 14:
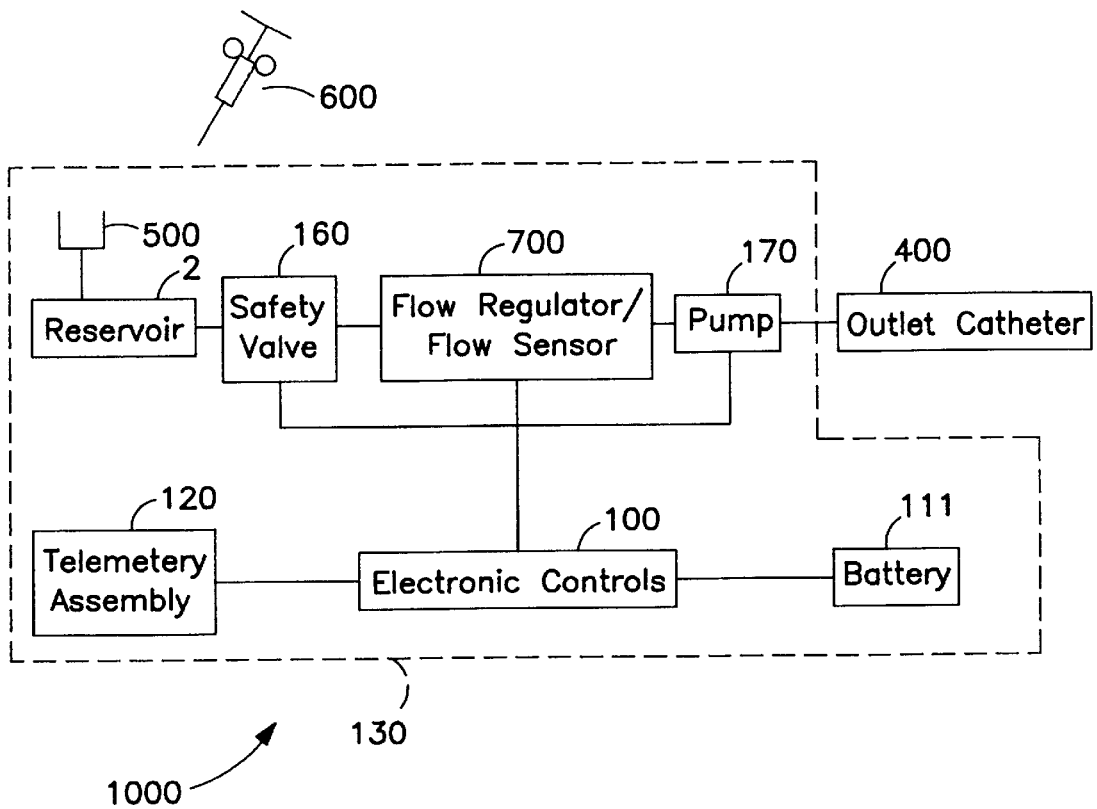
FIG. 14 is a block diagram of an alternative embodiment in which the present invention may be practiced.

FIG. 14 is a block diagram of an alternative embodiment in which the present invention may be practiced. This FIG. particularly shows an active pump drug infusion device. As seen, such a system 1000 comprises a reservoir 2, flow regulator/flow sensor 7000, electronic controls 100, battery 111, telemetry assembly 120 and outlet catheter 400. Flow regulator/flow sensor is coupled to the reservoir across safety valve 160 and further coupled to the outlet catheter across pump 170. Flow regulator/flow sensor regulates the flow of material which may be transmitted from the reservoir to the outlet catheter by pump in a manner to the flow regulator already described above, i.e. it regulates flow such that flow rate is independent of reservoir pressure within a given pressure range. Moreover, in this embodiment, the flow regulator also functions as a flow sensor to permit the flow rate to be sensed such that the device can track how much drug is delivered. Further, this component also permits the device to test itself so as to check and monitor the actual flow rate. As already described above, the system may be refilled through injection port 500 through the use of a needle 600 as is well known. Surrounding all components of the implantable pump other than the outlet catheter is a hermetic closure 130 as is well known in the art. Electronic controls 100, battery 111, telemetry assembly 120 and pump 170 are all constructed in any manner well known in the art. Electronic controls are powered by battery and may receive remote operation instructions via telemetry assembly, as is well known in the art. Safety valve is preferably of a design as shown in the co-pending application of Haller et al. "Implantable Infusion Device Having Safety Valve" (P-7356) assigned to the assignee of the present invention and incorporated herein by reference.

Figure 15:
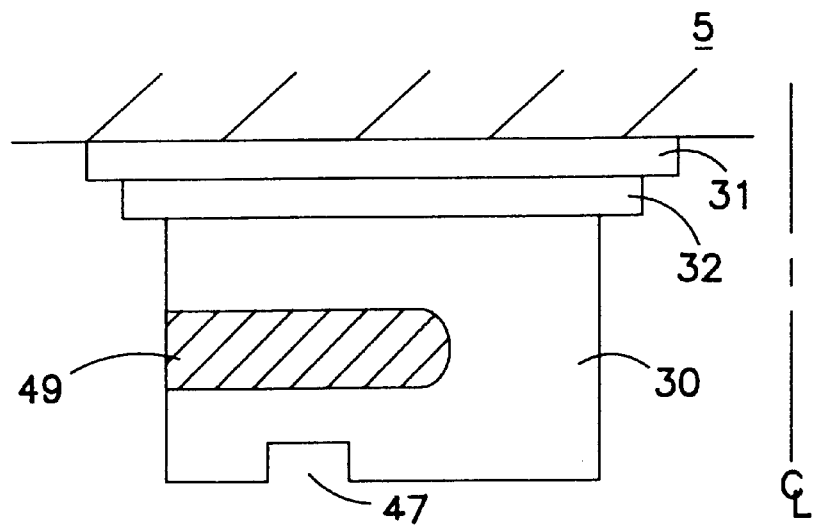
FIG. 15 shows, in isolation, an alternative embodiment for docking structure which may be used in the present invention.

FIG. 15 shows, in isolation, an alternative embodiment for docking structure which may be used in the present invention. As seen, this embodiment is substantially similar to that already shown in FIG. 11, but for the fact that groove is filled in with a material 49 which will assist with isolation of thermal stresses created at the bottom surface of the docking station 30. Material, preferably is a ceramic, although materials may also be used.

Figure 16:
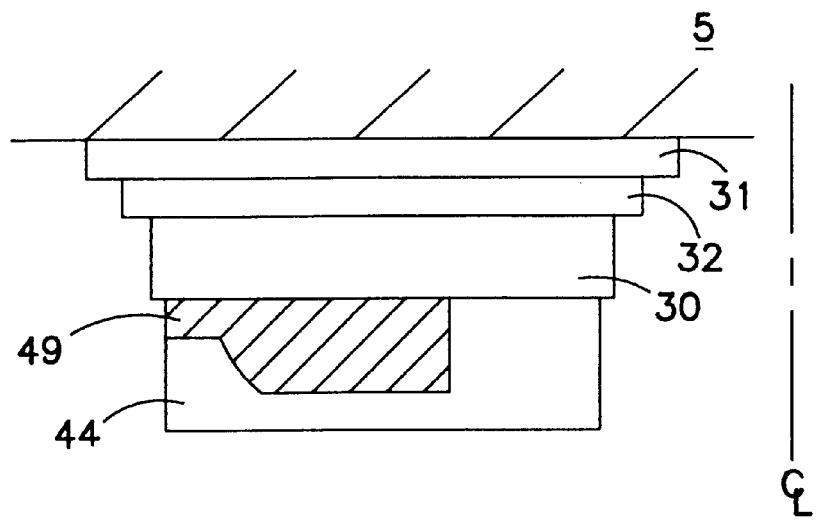
FIG. 16 shows, in isolation, an alternative embodiment for docking structure which may be used in the present invention.

FIG. 16 shows, in isolation, an alternative embodiment for docking structure which may be used in the present invention. As seen, this embodiment is substantially similar to that already shown in FIG. 15, but for the fact that groove which is filled in with a material 49 which will assist with the thermal isolation of the bottom surface of the docking station 30 is non-symmetrical in shape. Namely this groove is fashioned so as to have an overhang 44. Material 49 may be a ceramic or any other suitable and acceptable material which will assist in the thermal isolation of bottom surface and the weld join from the top surface. Although this embodiment is shown with its groove filled in with a material, it should be understood the overhang type groove may also be practiced without being filled in with additional material.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An implantable drug infusion device comprising:
   a hermetic enclosure;
   a drug reservoir positioned within the hermetic enclosure,
   a drug handling component, the drug handling component joined with the drug reservoir by a welded joint; and
   means for isolating the thermal stresses created during the formation of the welded joint used to join the drug reservoir and the drug handling component.

2. The implantable drug infusion device of claim 1 wherein the means for isolating the thermal stresses created during the formation of the welded joint comprises a docking station means.

3. The implantable drug infusion device of claim 2 the docking station means having a groove.

4. The implantable drug infusion device of claim 3 wherein the groove is rectangular.

5. The implantable drug infusion device of claim 3 wherein the groove is spoon shaped.

6. The implantable drug infusion device of claim 3 wherein the groove is club-shaped.

7. The implantable drug infusion device of claim 3 wherein the groove is a V-groove.

8. The implantable drug infusion device of claim 3 the docking station further having means for aligning the drug reservoir with the docking station.

9. The implantable drug infusion device of claim 8 wherein the means for aligning the drug reservoir with the docking station comprise a groove.

10. An implantable drug infusion device comprising:
    a hermetic enclosure;
    a first member positioned within the hermetic enclosure;
    a second member positioned within the hermetic enclosure, the second member having a top planar surface and a bottom planar surface, the first member joined to the top planar surface of the second member; and
    a third member positioned within the hermetic enclosure, the third member joined to the bottom planar surface of the second member by a weld joint, the second member having means for isolating the thermal stresses created during the formation of the weld joint away from the top planar surface.

11. The implantable drug infusion device of claim 10 wherein means for isolating the thermal stresses created during the formation of the weld joint away from the top planar surface comprises a groove.

12. The implantable drug infusion device of claim 11 wherein the groove is within the second member between the top planar surface and the bottom planar surface.

13. The implantable drug infusion device of claim 11 wherein the groove is within the second member equally between the top planar surface and the bottom planar surface.

14. The implantable drug infusion device of claim 13 wherein the groove is rectangular.

15. The implantable drug infusion device of claim 13 wherein the groove is spoon shaped.

16. The implantable drug infusion device of claim 13 wherein the groove is club-shaped.

17. The implantable drug infusion device of claim 13 wherein the groove is a V-groove.

18. The implantable drug infusion device of claim 10 the second member further having means for aligning the third member with the second member.

19. The implantable drug infusion device of claim 18 wherein the means for aligning the third member with the second member comprise a groove.

20. The implantable drug infusion device of claim 19 wherein the groove is located in the bottom surface of the second member.

* * * * *